US008292856B2

(12) United States Patent
Bertrand et al.

(10) Patent No.: US 8,292,856 B2
(45) Date of Patent: Oct. 23, 2012

(54) IMPLANTABLE CEREBRAL SPINAL FLUID DRAINAGE SYSTEM

(75) Inventors: William J. Bertrand, Ventura, CA (US);
Derek J. Harper, Prescott, AZ (US);
Lori Cone Speckman, Ventura, CA (US); Andrew R Kiehl, Oak View, CA (US); Ron D Scheer, Burlington, MA (US)

(73) Assignee: Medtronic, Inc., Minneapolis, MN (US)

( * ) Notice: Subject to any disclaimer, the term of this patent is extended or adjusted under 35 U.S.C. 154(b) by 562 days.

(21) Appl. No.: 11/736,887

(22) Filed: Apr. 18, 2007

(65) Prior Publication Data

US 2008/0097276 A1 Apr. 24, 2008

Related U.S. Application Data

(62) Division of application No. 11/185,530, filed on Jul. 20, 2005, now Pat. No. 7,309,330.

(60) Provisional application No. 60/590,022, filed on Jul. 20, 2004.

(51) Int. Cl.
*A61M 1/00* (2006.01)
*A61M 5/00* (2006.01)

(52) U.S. Cl. ............... 604/317; 604/8; 604/9; 604/10; 604/323

(58) Field of Classification Search ............ 604/317, 604/8, 9, 10, 128, 323
See application file for complete search history.

(56) References Cited

U.S. PATENT DOCUMENTS

| | | | |
|---|---|---|---|
| 3,492,996 A | 2/1970 | Fountain | |
| 3,901,245 A * | 8/1975 | Spitz et al. | 604/10 |
| 4,240,434 A * | 12/1980 | Newkirk | 604/9 |
| 4,692,147 A | 9/1987 | Duggan | |
| 4,731,056 A * | 3/1988 | Tremulis | 604/118 |
| 4,795,437 A * | 1/1989 | Schulte et al. | 604/10 |
| 5,164,583 A | 11/1992 | Aichinger et al. | |
| 5,182,624 A | 1/1993 | Tran et al. | |
| 5,207,661 A * | 5/1993 | Repschlager | 604/317 |
| 5,331,166 A | 7/1994 | Yamamoto et al. | |
| 5,448,613 A | 9/1995 | Haendle et al. | |
| 5,751,783 A | 5/1998 | Granfors et al. | |
| 5,777,335 A | 7/1998 | Mochizuki et al. | |
| 5,877,501 A | 3/1999 | Ivan et al. | |
| 5,937,027 A | 8/1999 | Thevenin et al. | |
| 5,980,480 A | 11/1999 | Rubenstein et al. | |
| 6,075,256 A | 6/2000 | Kaifu et al. | |
| 6,198,800 B1 | 3/2001 | Garland et al. | |
| 6,208,710 B1 | 3/2001 | Nagai | |
| 6,243,441 B1 | 6/2001 | Zur | |
| 6,264,625 B1 | 7/2001 | Rubenstein et al. | |
| 6,323,490 B1 | 11/2001 | Ikeda et al. | |

(Continued)

OTHER PUBLICATIONS

Nilsson, C. et al., "Circadian Variation in Human Cerebrospinal Fluid Production Measured by Magnetic Resonance Imaging", Am. J. Physiol Regul Integr Comp Physiol, vol. 262: R20-R24, 1992.

(Continued)

*Primary Examiner* — Tatyana Zalukaeva
*Assistant Examiner* — Ginger T Chapman
(74) *Attorney, Agent, or Firm* — IPLM Group, P.A.

(57) ABSTRACT

Drainage system including a ventricular catheter, a drainage catheter, and a positive displacement pump that can function to actively drain CSF from the ventricles of the brain of a patient. Methods of using a drainage system in accordance with the invention are also disclosed, as well as kits.

16 Claims, 3 Drawing Sheets

U.S. PATENT DOCUMENTS

| | | |
|---|---|---|
| 6,353,228 B1 | 3/2002 | Itabashi |
| 6,404,851 B1 | 6/2002 | Possin et al. |
| 6,423,973 B2 | 7/2002 | Choo et al. |
| 6,515,286 B2 | 2/2003 | Kuwabara |
| 6,572,583 B1 | 6/2003 | Olsen et al. |
| 6,585,677 B2 * | 7/2003 | Cowan et al. ............ 604/9 |
| 6,643,411 B2 | 11/2003 | Nonaka |
| 6,689,085 B1 | 2/2004 | Rubenstein et al. |
| 6,895,078 B2 | 5/2005 | Alving et al. |
| 6,979,351 B2 | 12/2005 | Forsell et al. |
| 7,025,742 B2 | 4/2006 | Rubenstein et al. |
| 2001/0028701 A1 | 10/2001 | Schulz |
| 2002/0054659 A1 | 5/2002 | Okumura et al. |
| 2002/0087111 A1 | 7/2002 | Ethier et al. |
| 2002/0101960 A1 | 8/2002 | Nokita |
| 2002/0109097 A1 | 8/2002 | Tashiro |
| 2003/0004495 A1 | 1/2003 | Saul |
| 2004/0030279 A1 | 2/2004 | Rubenstein et al. |
| 2004/0098113 A1 * | 5/2004 | Forsell et al. ............ 623/1.25 |
| 2004/0147874 A1 | 7/2004 | Kliem et al. |
| 2005/0096582 A1 | 5/2005 | Burnett |

OTHER PUBLICATIONS

Matthews, Ernest S. et al., "A Preliminary report on a Biological Fluid Transfer System for the Treatment of Hydrocephalus", Department of Neurosurgery, New York School of Medicine, pp. 103-107.

Matthews, Ernest S. et al., "A Volume Control System for the Treatment of Hydrocephalus", Department of Neurosurgery, New York School of Medicine, p. 417.

Silverberg, Gerald D., "Normal Pressure Hydrocephalus (NPH): Ischemia, CSF stagnation or both", Brain, vol. 127, No. 5, pp. 947-948, 2004.

International Search Report for PCT/US2005/025783.

* cited by examiner

IMPLANTABLE CEREBRAL SPINAL FLUID DRAINAGE SYSTEM

RELATED APPLICATIONS

This application claims priority from U.S. Provisional Application No. 60/590,022, filed on Jul. 20, 2004, entitled "SMART SHUNT"; and from U.S. patent application Ser. No. 11/185,530, filed Jul. 20, 2005, entitled Implantable Cerebral Spinal Fluid Drainage Device and Method of Draining Cerebral Spinal Fluid.

FIELD OF THE INVENTION

This invention relates generally to implantable fluid drainage devices and, more particularly, to such devices for draining cerebral spinal fluid.

BACKGROUND OF THE INVENTION

Ventricles of the brain contain cerebral spinal fluid (CSF) that cushions the brain against shock. Cerebral spinal fluid is constantly being secreted and absorbed by the body. Cerebral spinal fluid is produced in the ventricles of the brain, where under normal conditions it is circulated in the subarachnoid space and reabsorbed into the bloodstream, predominantly via the arachnoids villi attached to the superior sagittal sinus. In a normal, healthy person, the secretion and absorption of cerebral spinal fluid is in equilibrium for the most part. However, if blockages of the circulation of cerebral spinal fluid are created, in the ventricles for example, cerebral spinal fluid can't be reabsorbed by the body at the proper rate and it can build up in the ventricles.

This can create a condition known as hydrocephalus which is marked by an excessive accumulation of fluid violating the cerebral ventricles and then the brain. Hydrocephalus is a condition characterized by abnormal flow, absorption, or formation of cerebral spinal fluid within the ventricles of the brain which subsequently increases the volume and pressure of the intracranial cavity. The condition can cause a separation of the cranial bones. If left untreated, the increased intracranial pressure can lead to neurological damage and may result in death.

Over the past 40 years, a common treatment for hydrocephalus patients has been to implant a cerebral spinal fluid shunt. The standard shunt consists of a ventricular catheter, a valve and a distal catheter. The ventricular catheter is tunneled into the brain through a burr hole in the skull and placed into ventricles to shunt cerebral spinal fluid to other areas of the body. The excess cerebral spinal fluid is typically passively drained from the ventricles to a suitable cavity, for example the peritoneum or the atrium, where it can be reabsorbed. The shunt relieves the pressure from the cerebral spinal fluid on the brain, thereby lessening or managing the symptoms.

Current cerebral spinal fluid shunts all act in a passive manner, which provides only approximate control of cerebral spinal fluid drainage pressure and volume. More accurate control of cerebral spinal fluid drainage could alleviate symptoms of shunted patients and assist in the management of hydrocephalus.

BRIEF SUMMARY OF THE INVENTION

The invention provides a drainage system that includes a ventricular catheter, a drainage catheter, and a positive displacement pump that can function to actively drain CSF from the ventricles of the brain of a patient, the pump can include, for example, a diaphragm pump, a piston pump, a rotor pump, a peristaltic pump, or a screw pump.

In one embodiment, an effect of the pump is controlled based at least in part on monitoring of symptoms or changes in symptoms of the patient, the time of day, circadian rhythms of the patient, the occurrence of various sleep patterns, the cardiac cycle, an accelerometer that is monitoring the patient, the intracranial pressure of the patient, a siphon control device or some combination thereof.

Another embodiment of the invention provides a drainage system that includes a ventricular catheter, a drainage catheter, a siphon control device, a bypass, a bypass valve and a positive displacement pump that can function to actively drain CSF from the ventricles of the brain of a patient, wherein the siphon control device actuates the bypass valve which effects flow through the bypass when an overdrainage condition of the ventricles is detected and through the distal catheter when the overdrainage condition has been mitigated.

DETAILED DESCRIPTION OF THE INVENTION

The entire content of provisional U.S. Provisional Application Ser. No. 60/590,022, filed Jul. 20, 2004, and U.S. application Ser. No. 11/185,530, filed Jul. 20, 2005 are hereby incorporated by reference.

The invention provides a cerebral spinal fluid shunt that functions to actively drain cerebral spinal fluid from the ventricles of the brain to some other suitable cavity. The active draining is accomplished by including a pump in the cerebral spinal fluid shunt or drainage system. Generally, suitable cavities can include, but are not limited to the peritoneum and the atrium. Drainage systems of the invention can be used for the treatment of hydrocephalus, acute conditions, or both.

Figure 1:
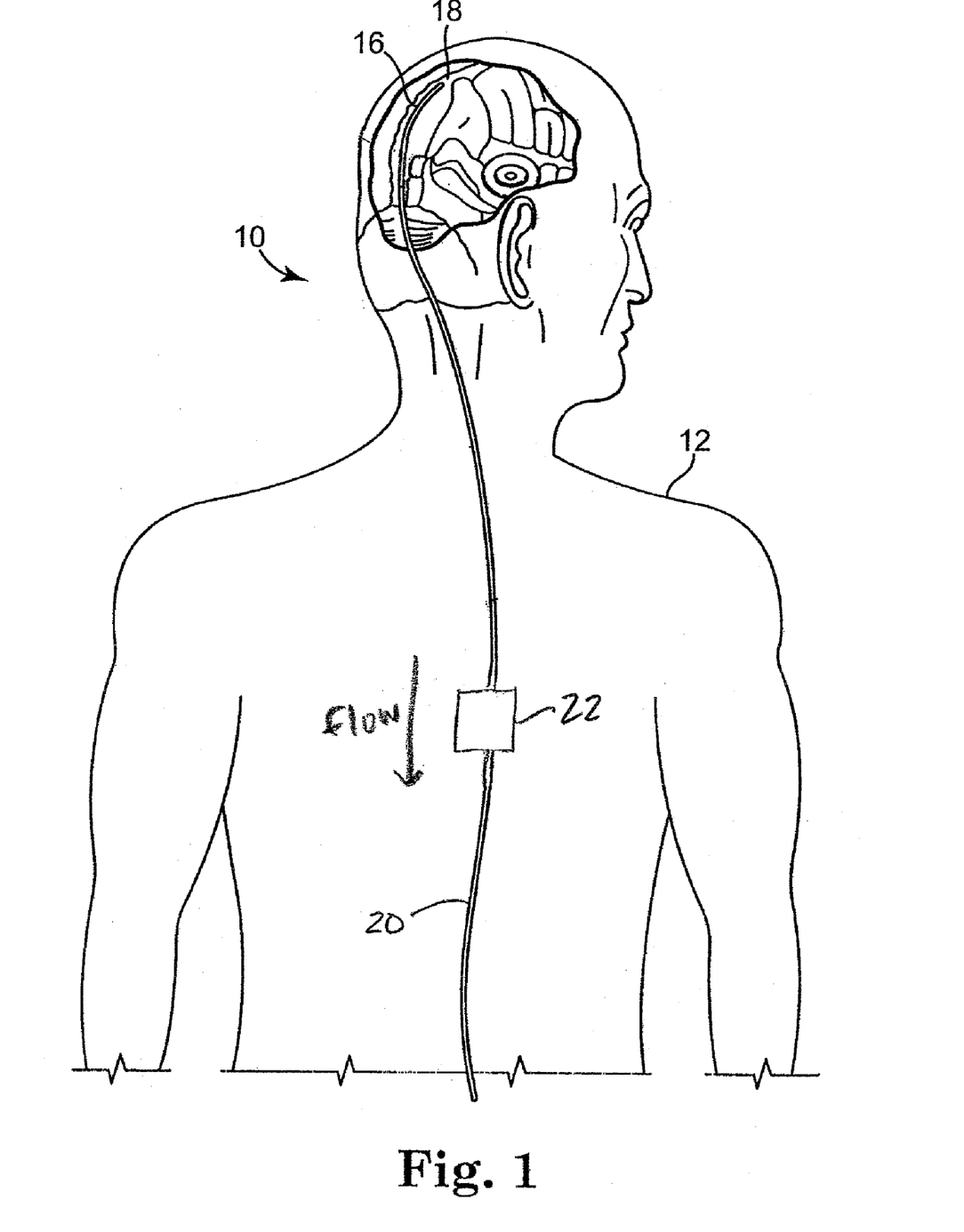
FIG. 1 is a cut-away perspective view of a drainage system in accordance with an embodiment of the invention implanted into the cranium of a patient.

FIG. 1 illustrates an embodiment of a cerebral spinal fluid shunt, or drainage, system 10 for draining cerebral spinal fluid from one area, for example, the ventricles of the brain, of the body of patient 12, to another area of the body of patient 12. Cerebral spinal fluid can be drained to the peritoneum and/or atrium and, alternatively, to the sagittal sinus. Shunt system 10 may include a ventricular catheter 16, a drainage catheter 20, and a pump 22.

Ventricular catheter 16, having a lumen, connects has an inlet location 18 in the ventricle of patient 12. It is to be recognized and understood that other locations, other than inlet location 18 in the ventricle, can be utilized. Distal catheter 20 includes an outlet (not shown in FIG. 1) for cerebral spinal fluid which can be located in the peritoneum. Ventricular catheter 16 and distal catheter 20 can be configured as is generally known to those of skill in the art. It is to be recognized and understood that other outlet locations can also be utilized. Examples of other possible outlet locations include the atrium and the sagittal sinus.

In one embodiment of a shunt system 10 in accordance with the invention, the pump 22 can be located in the patient 12 at a location that is removed from the brain. Embodiments such as this may offer advantages because the patient's head would be free of implant related artifacts during CT scans or MRI imaging. In one embodiment, the pump 22 is located within the torso of the patient. Examples of possible locations for the pump 22 include, but are not limited to the chest and the abdomen of the patient. The pump 22 is placed within the drainage system 10 and oriented to pump from cerebral spinal fluid from the ventricular catheter 16 and towards the distal catheter 20. When a drainage system 10 of the invention is implanted into a patent, this will have the effect of pumping cerebral spinal fluid from the ventricles and into the drainage location within the patient.

The pump 22 is generally a positive displacement pump. Positive displacement pumps are generally categorized as reciprocating pumps, metering pumps or rotary pumps. Generally, positive displacement pumps operate by forcing a fixed volume of fluid from the inlet pressure section of the pump into the discharge zone of the pump. Specific examples of types of pumps can include, but are not limited to, a diaphragm pump, piston pump, rotor pump, peristaltic pump, screw pump, or other suitable types of pumps as is known to those of skill in the art. In one embodiment of the invention, a peristaltic pump is utilized as the pump 22 of the drainage system 10.

Generally, pumps that have a capacity from about 1 mL/hr to about 200 mL/hr can be utilized in drainage systems 10 of the invention. In another embodiment, pumps that have a capacity from about 1 mL/hr to about 50 mL/hr can be utilized in drainage systems 10 of the invention. In yet another embodiment, pumps that have a capacity from about 10 mL/hr to about 30 mL/hr can be utilized in drainage systems of the invention. In one embodiment, a constant speed positive displacement pump can be utilized in a drainage system of the invention. In another embodiment, a variable speed positive displacement pump can be utilized in a drainage system of the invention.

Generally, pumps 22 that are used in drainage systems 10 of the invention include a power source. The power source may take the form of a small battery. An external source of inductively coupled power may be used, in some embodiments, to power some features of the pump, or to recharge the battery. For example, pump 22 may include an inductive power interface for transcutaneous inductive power transfer to power some of the functions of the pump. However, pump 22 typically will include a small battery cell within the housing of the pump. Alternatively, pump 22 may include an inductive power interface in lieu of a battery.

In further embodiments, the power source for the pump 22 may be rechargeable via electromagnetic induction or ultrasonic energy transmission, and includes an appropriate circuit for recovering transcutaneously received energy. For example, the power source may include a secondary coil and a rectifier circuit for inductive energy transfer. In still other embodiments, the power source may not include any storage element, and the pump may be fully powered via transcutaneous inductive energy transfer, which may be provided by an external receiver.

In some embodiments, pump 22 is capable of wireless communication. Wireless communication can be utilized to transmit a number of parameters associated with the pump 22, including, but not limited to, the current settings of the pump 22, previous settings of the pump 22, the elapsed time since implantation of the pump 22, expected battery life of the pump 22, and battery consumption of the pump 22 for example. Wireless communication could also be utilized to interrogate and change the programming of the pump 22.

In embodiments that are capable of wireless communication, a telemetry interface permits wireless communication of the pump 22 with an external programmer for wireless transmission of information from the pump 22, as well as wireless reception of activation triggers that direct the pump 22 to change a function thereof.

In one embodiment, there can be wireless communication between a device that is monitoring the at least one control factor (referred to hereafter as a "monitoring device") and the pump 22. There can also be wireless communication between a monitoring device and a programmer. In one embodiment there could also be wireless communication between the programmer and the pump 22. the communication between the programmer and the pump 22 could either be automatic or could be initiated, using the programmer, by a physician or patient, or automatic for some types of communication and initiated for other types of communication. The use of a programmer could allow a physician to interrogate the pump, as well as the one or more monitoring devices, in order to gain a better understanding of the control factors, the pump parameters, and any possible interplay between the two.

As a further alternative to wireless communication, triggered activation may be applied by the patient 12 or a physician in the form of a magnet swiped in proximity to the pump 22, in which case the pump 22 will include appropriate sensing circuitry to detect the magnet.

In some embodiments, the pump 22 can include one or more processors that can carry out a number of functions, including, but not limited to, controlling the telemetry interface, monitoring and controlling the parameters of the pump, and processing and storage of information from an external programmer. The processor can control operation of the pump 22 and may include one or more microprocessors, digital signal processors (DSPs), application-specific integrated circuits (ASICs), field-programmable gate arrays (FPGAs), or other equivalent logic circuitry. The pump 22 may also include memory, which can include any magnetic, electronic, or optical media, such as random access memory (RAM), read-only memory (ROM), electronically-erasable programmable ROM (EEPROM), flash memory, or the like, or a combination thereof. The pump's memory may store program instructions that, when executed by the pump's processor, cause the controller to perform the functions ascribed to it herein. For example, the memory may store instructions for the processor to execute in support of control of a wireless telemetry interface and control of, and processing of information from an external programmer. The pump's memory may include separate memories for storage of instructions and functioning of the pump 22.

Examples of pumps that can be utilized as pump 22 in a drainage system 10 in accordance with the invention include, but are not limited to the pump component of the SYNCHROMED II® Programmable Pump, the SYNCHROMED EL® Programmable Pump, or the SYNCHROMED® Programmable Pump, all of which are commercially available from Medtronic, Inc. (Minneapolis, Minn.).

In a drainage system of the invention, the effects of the pump 22 are controlled. As used herein, control of the effects of the pump can include, for example the rate the pump is pumping, whether the pump is cycled on and off, the timing of when the pump is cycled on and off, and any accelerations or decelerations of the pumping rate. Control of the pump 22 can also include controlling an effect of the pump 22 while not altering its rate or whether it is on or off. Controlling the effects of the pump can include simple control of the pump itself, programming the pump, or controlling the effects of the pump on the drainage system as a whole. As used herein, "controlling the pump" or "control of the pump" refers more generally to controlling the effects of the pump as discussed broadly in this specification.

Controlling the pump 22 can be done based on one of a number of different factors or any combination thereof. These different factors include, but are not limited to, monitoring of symptoms or changes in symptoms of the patient, the time of day, circadian rhythms of the patient, the occurrence of various sleep patterns, the cardiac cycle, an accelerometer that is monitoring the patient, the intracranial pressure of the patient, and a siphon control device. The at least one factor that can be used, at least in part, to control the pump 22, is generally referred to herein as a control factor or control factors. The relevant control factor or control factors can be monitored before the drainage system 10 is implanted in the patient, after the implantation of the drainage system 10 or some combination thereof.

In embodiments where symptoms or changes in symptoms are monitored, the monitoring can be as simple as the patient monitoring and recording the symptoms and when the they are occurring by hand. In another embodiment, the symptoms, the severity of the symptoms, the time of onset, the duration, and other details regarding the symptoms can be recorded by the patient. In another embodiment, the patient would be provided with a device for electronically recording the symptoms. Examples of devices for recording the symptoms include, but are not limited to a patient programmer, a personal data assistant (PDA), or some similar device. In some embodiments the device for recording the symptoms can communicate with a physician programmer or a physician workstation. In some embodiments, communication can be accomplished wirelessly, and in other embodiments, a physical connection can be utilized. In some embodiments, a physician programmer or physician workstation can automatically interrogate the patient programmer at predetermined time intervals via wireless communication.

Symptoms that can be monitored include, but are not limited to ventricular size, cerebral spinal fluid flow rate, patient activity, gate, body temperature, continence, mental function, and water content of the brain for example. In another embodiment, cerebral spinal fluid flow rate, ventricular size, or some combination thereof are monitored and recorded.

In embodiments where the time of day is considered in programming the pump, the pump can include an internal clock that is programmed upon implantation for example. One example of programming that is based at least in part, on the time of day would include a 24 hour drainage profile. An exemplary 24 hour drainage profile may have a different pumping rate during the night than the day. Another exemplary 24 hour drainage profile may shut the pump off during different points in a 24 hour period. The pump can be shut off, or slowed down, for example at times during the day that biologically relevant or beneficial. Examples of times of the day that may be biologically relevant or beneficial may include, but are not limited to, the time a patient goes to bed or wakes up.

In another embodiment a 24 hour drainage profile could be created that is independent of the particular patient. In yet another embodiment, a 24 hour drainage profile could be created that is patient dependent. In such an embodiment, data could be gathered regarding the patient, such as for example, the normal bed time of the patient and the normal waking time of the patient. That information could then be used to set the 24 hour drainage profile. In another embodiment, either a patient independent or patient dependent 24 hour drainage profile could be modified based on a number of different factors, including but not limited to patient symptoms and changes in the patient's daily routine.

Another 24 hour drainage profile would allow the patient to dictate, at least in part, the programming by indicating when the patient was going to bed, and waking up for example. Such an embodiment may be programmed for example, by imposing that the pump be turned on, or the rate increased when the patient indicates that he or she is going to sleep. Similarly, it could be imposed that the pump be turned off, or the rate decreased when the patient indicates that he or she is waking up.

In some embodiments, Circadian rhythms are considered in programming the pump. Circadian rhythms generally refer to the endogenous internal clock that controls many biological functions, having a periodicity of about 24 hours. A similar 24 hour time frame is also seen in fluctuations in endocrinal secretions, core body temperatures and cognitive performance. The production of CSF also has a circadian variation in that there is an increase in nocturnal production that can reach twice the daytime values. Some data suggests that a maximum value of production is reached at about 0200 hours and a minimum level of production is reached at about 1800 hours (Nilsson, C. et al., *Am. J. Physiol.* 1992; 262; R20-R24).

Therefore, in one embodiment, the pump rate could be increased to correspond approximately with the maximum production of CSF. In another embodiment, the pump rate could be decreased to correspond approximately with the minimum production of CSF. In yet another embodiment, the pump could be turned on or off to correspond with the maximum or minimum CSF production respectively. In a further embodiment some combination of the above circadian rhythm based controls could be utilized in the programming.

In one embodiment, the pump can be programmed, based on, at least in part, the occurrence of random eye movement (REM) sleep. For example, at least in patients with normal pressure hydrocephalus (NPH), CSF pressure displays waves of increased pressure during REM sleep (Silverberg, G., *Brain* 2004; 127; 947-948). Therefore, in one embodiment, the pump could be programmed to turn on or increase the pumping rate during the time of expected REM sleep. This timing could be patient independent or patient dependent in that the expected REM sleep time could be determined based on the normal bedtime of the patient.

In one embodiment, the pump could be programmed based, at least in part, on the cardiac cycle. It is known to those of skill in the art that CSF flows in a pulsatile nature that is synced, at least to some degree with the cardiac cycle. Therefore, in one embodiment the pump could rate could be lower with diastole and slightly higher with systole. In another embodiment the pump could be turned off with diastole and turned on with systole. This type of programming could be either patient independent, in that the interval is based on a "normal" heart rate, or patient dependent, in that the interval could be based on the normal heart rate of the particular patient. In yet another embodiment, the interval could be based on the patient's heart rate at the time. Such an embodiment could utilize and react to a sensor to detect heart rate.

In another embodiment, the programming of the pump could be based, at least in part, on the position of the patient. An example of a monitoring device for monitoring the position of the patient is an accelerometer that is associated with the patient. An accelerometer that is associated with a patient can monitor whether the patient is upright or lying down. In one embodiment, the pump could be turned on or the rate increased when the accelerometer indicates that the patient is lying down. In another embodiment, the pump could be turned off or the rate decreased when the accelerometer indicates that the patient is upright. In yet another embodiment, the pump could be switched on or off or the rate increased or decreased upon a predetermined delay after the accelerometer detects the patient lying down or upright. Such an embodiment could decrease switching or rate changing that could be associated with quick changes in the patient's position that may not be permanent. In another embodiment, the position of the patient could be monitored by the patient themselves and the pump controlled, at least in part, based on noted changes, by the patient, of position.

In another embodiment, the programming of the pump is based, at least in part, on intracranial pressure. In such an embodiment, the pump can be turned on or the rate increase when the intracranial pressure rises above a certain threshold. In another such embodiment, the pump can be turned off, or the rate decreased when the intracranial pressure falls below a certain threshold. In embodiments such as these, the change in the pump can also be affected upon a delay of a predetermined time after the intracranial pressure reaches or falls below a threshold pressure. In such an embodiment, for example, the intracranial pressure could be checked again after the delay period to determine if the threshold pressure was still met. The use of a delay and recheck may aid in avoiding switching or changing of the pump unnecessarily or in response to aberrant changes in intracranial pressure.

In another embodiment the programming is based, at least in part, on trends in intracranial pressure rather than absolute intracranial pressure. Such an embodiment could afford a system that affects a change in the pump based on an overall increase or decrease in intracranial pressure rather than momentary fluctuations, which may be entirely normal for the patient. An embodiment that responds to trends in intracranial pressure could, for example, affect a change in the pump control when an absolute change of intracranial pressure over a given time period is detected. For example, the pump could turn on or increase the rate of pumping when the intracranial pressure increases about 5 cm $H_2O$ or more over a period of about 1 hour. In another embodiment, the pump could turn off or decrease the rate of pumping when the intracranial pressure decreases about 5 cm $H_2O$ or more over a period of about 1 hour. In one embodiment a physician that is utilizing a drainage system of the invention in a patient would be able to select and/or modify the absolute pressure change that would effectuate a pump change.

Figure 2:
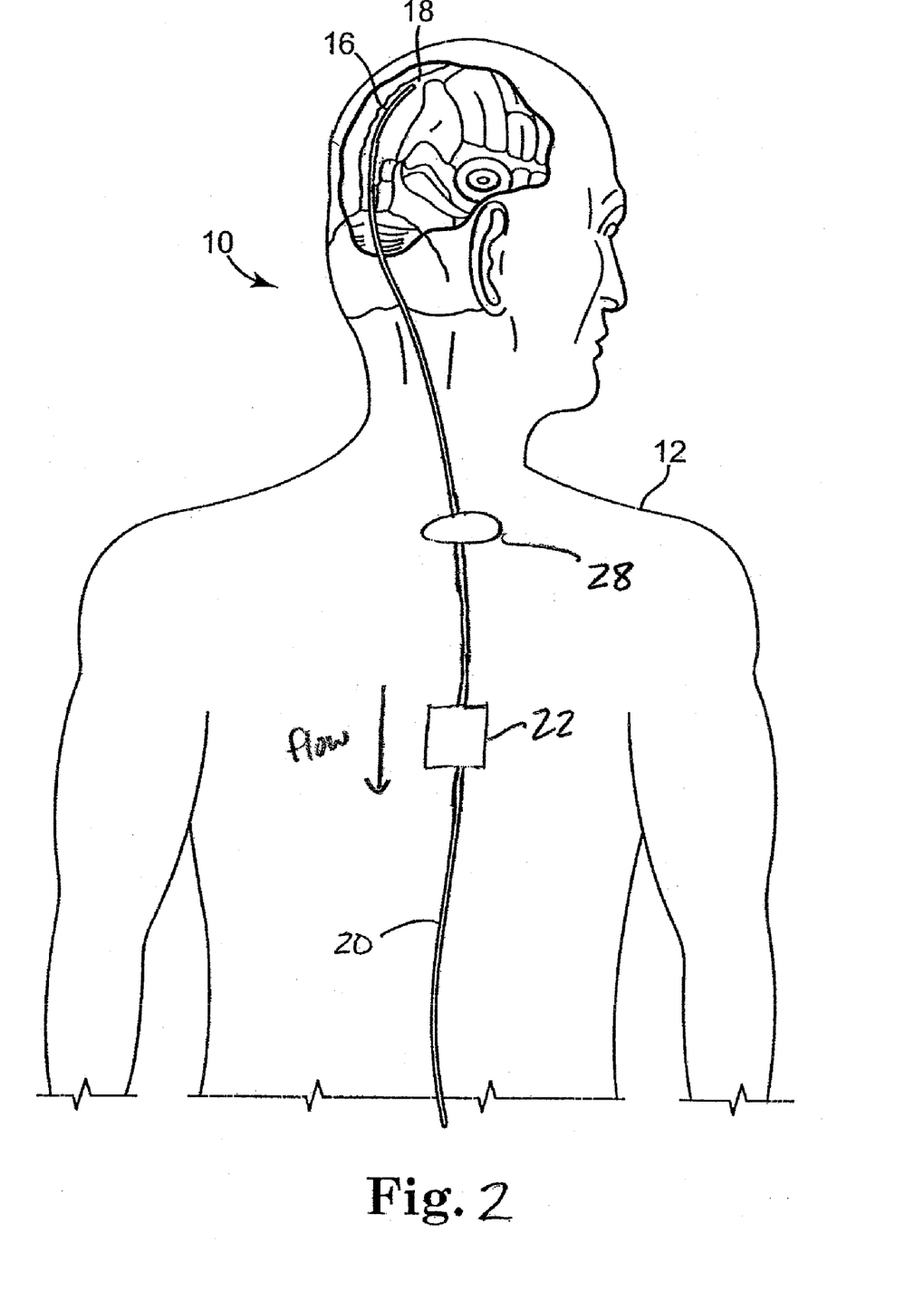
FIG. 2 is a cut-away perspective view of a drainage system in accordance with another embodiment of the invention implanted into the cranium of a patient.

Another factor that can be used to control the pump 22 is the degree of drainage of the ventricle(s). In one embodiment, the degree of drainage can be monitored by a siphon control device. FIG. 2 depicts another embodiment of a drainage system 10 that includes a monitoring device, which is a siphon control device 28. Siphon control devices, also referred to as anti-siphon devices are designed to minimize overdrainage of CSF and maintain intraventricular pressure within a normal physiological range, regardless of the patient's position. Siphon control devices are commercially available and one of skill in the art, could, given the teachings of this disclosure, incorporate a commercially available siphon control device into a shunt system of the invention. Examples of commercially available siphon control devices include, but are not limited to, the PS MEDICAL® DELTA® valve (Medtronic, Minneapolis, Minn.), the BEYERS-CHULTE® Anti-Siphon Device (Integra Neurosciences, Plainsboro, N.J.), and SIPHONGUARD™ Anti-Siphon Device (Codman, Raynham, Mass.).

The siphon control device 28 controls the pump 22 by stopping the pump or reducing the rate of pumping when overdrainage of the ventricle(s) is detected. The siphon control device 28 could control the pump 22 via a switch, which could be actuated when the siphon control device would normally close and open.

Figure 3:
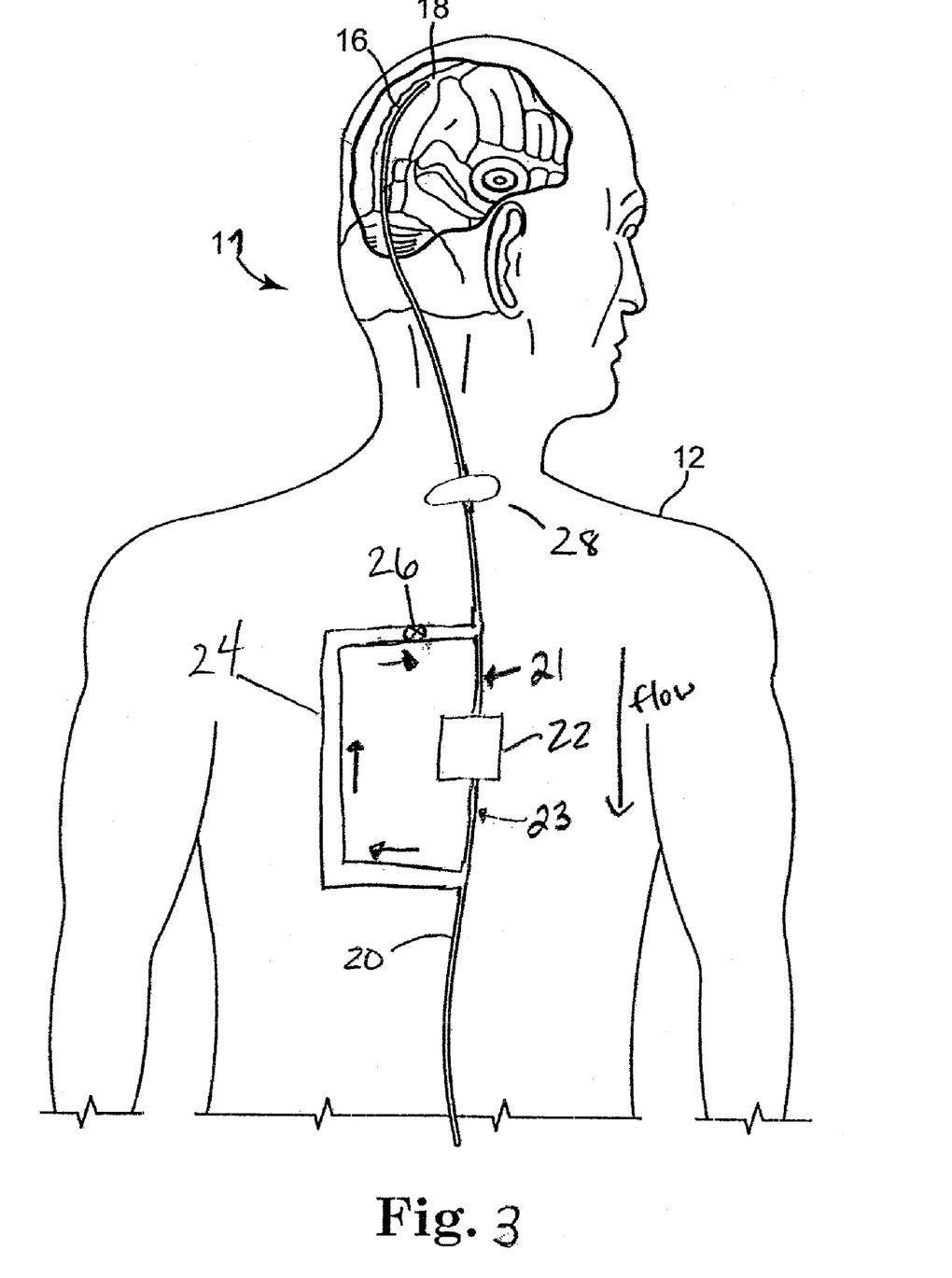
FIG. 3 is cut-away perspective view of a drainage system in accordance with a further embodiment of the invention implanted into the cranium of a patient.

Another embodiment of a drainage system 10 in accordance with the invention is depicted in FIG. 3. A drainage system 10 in accordance with this embodiment of the invention includes all the components of the embodiment depicted in FIGS. 1 and 2; a ventricular catheter 16, a distal catheter 20, a pump 22, and a siphon control device 28; and also includes a bypass 24, and a bypass valve 26. In such an embodiment, the bypass 24, bypass valve 26, and the siphon control device 28 can function to prevent or reduce overdrainage of the ventricle or ventricles of the patient 12. As seen in FIG. 3, the bypass directs flow from the outlet area 23 of the pump 22 to the inlet area 21 of the pump 22. The bypass valve 26 can be located at any position within the bypass 24

The bypass 24 can be constructed of the same material as the ventricular catheter, and/or distal catheter. In one embodiment, the bypass 24 is constructed of tubing that is made of the same material and has the same outer diameter and inner diameter as the distal catheter 20. In one embodiment, the bypass and the bypass valve would be integrally formed with or within the pump itself and may not include an external tubing circuit. In one embodiment, the bypass could be a molded pathway in the pump housing material. Such a design may provide advantages such as being more compact, reliable, and simpler to implant and manufacture. Components that can be utilized as the bypass valve 26 are well known to those of skill in the art, having read this specification. For example, simple one way check valves, such as a ball and cone type can be utilized. Examples of commercially available valves that can be utilized as bypass valve 26 include, but are not limited to ball and cone check valves, membrane valves, diaphragm valves, and other types of valves known to those of skill in the art. The siphon control device 28 can be the same as that depicted in FIG. 2 above.

In this embodiment, the siphon control device 28 acts to open the bypass valve 26 when the siphon control device 28 detects overdrainage of the ventricle(s); and closes the bypass valve when the overdrainage is no longer detected. Therefore, when overdrainage is detected, the siphon control device 28 will close, preventing further drainage from the ventricle(s) via the ventricular catheter 16. The closing of the siphon control device 28 can also effectuate the opening of the bypass valve 26, which will control the pump by causing the pump to pump the existing fluid within the system through the bypass 24 instead of pumping further cerebral spinal fluid from the ventricle(s). Once the siphon control device 28 no longer detects the overdrainage condition, i.e. more cerebral spinal fluid is produced than is absorbed naturally, the siphon control device 28 will open, which will effectuate the bypass valve 26 to close. Once this happens, the pump 22 will once again continue to pump the excess cerebral spinal fluid from the ventricle(s).

An embodiment such as this may be advantageous in that it can provide a method to control a pump that runs continuously without the need to change the rate in response to certain conditions. Such an embodiment may allow the use of a simpler, more inexpensive pump and/or allow for less control mechanisms (i.e. software). Such an embodiment may also serve to extend the lifetime of the pump because it will not be switched on and off on a regular basis, which can often lead to the failure of the switching mechanism.

In one embodiment, a monitoring device can be used to monitor the at least one control factor. The type of monitoring device that can be used depends at least in part on the particular control factor or control factors that are being monitored.

In one embodiment, one monitoring device is utilized, and in another embodiment, more than one monitoring device is used. The monitoring device or devices can, but need not, be physically connected or in association with the drainage system. In one embodiment for example, a monitoring device can be in physical association with the ventricular catheter. Such an embodiment may be useful for monitoring intracranial pressure of the patient. In another embodiment, the monitoring device may not even be physically associated with the patient. For example, a monitoring device for monitoring symptoms of a patient could include a handheld device that allows the patient to input information about their symptoms. In some embodiments more than one monitoring device can be utilized to monitor more than one type of control factor. In another embodiment, more than one monitoring device can be used to monitor only one type of control factor. For example, tow accelerometers in association with the patient could be used to monitor the position of the patient.

The invention also offers a method of controlling flow of cerebral spinal fluid in a patient that includes the steps of implanting a drainage system of the invention in a patient, monitoring one or more control factors of the patient, and controlling the pump of the drainage system based at least in part on the results of monitoring at least one control factor.

A drainage system in accordance with the invention can be implanted as is known to those of skill in the art. In an embodiment where the drainage system is to be drained into the peritoneum, the surgical procedure to implant a drainage system may begin by placing a patient under general anesthesia, shaving their scalp is shaved and scrubbing the patient with an antiseptic from the scalp to the abdominal area. These steps can be taken in order to reduce the chances of an infection. Incisions can then be made on the head and in the abdomen to allow the neurosurgeon to pass the tubing of the drainage system through the fatty tissue just under the skin. A small hole is then made in the skull, opening the membranes between the skull and brain to allow the ventricular catheter 16 of the drainage system 10 to be passed through the brain and into the lateral ventricle. The distal catheter 20 is passed into the abdominal cavity through a small opening in the lining of the abdomen where the excess CSF will eventually be reabsorbed. The incisions are then closed and sterile bandages are applied. The pump 22 of the drainage system can be implanted within a pocket in the abdominal wall in such an embodiment.

As used herein, control factors refer to the factors that may be used to control the effects of the pump, including, but not limited to monitoring symptoms or changes in symptoms of the patient, the time of day, circadian rhythms of the patient, the occurrence of various sleep patterns, the cardiac cycle, an accelerometer that is monitoring the patient, the intracranial pressure of the patient, a siphon control device, or some combination thereof.

The results of monitoring the control factors are then used to control the pump. For example, the results that were obtained when monitoring the control factors can dictate for example, that the pump be turned off, turned on, the rate decrease, or the rate increased; or the bypass valve opened, or closed. In some embodiments, a processor in association with the pump controls the pump in light of the control factors that were monitored. In another embodiment, for example, with a siphon control device, the siphon control device automatically effectuates the bypass valve to control the pump.

Another embodiment of the invention is a kit that includes a ventricular catheter, a drainage catheter, and a positive displacement pump, wherein the components are assembled to form a drainage system that functions to actively drain CSF from the ventricles of the brain of a patient when implanted in a patient, and wherein the pump is controlled based at least in part on at least one control factor. Another embodiment of the invention includes a ventricular catheter, a drainage catheter, a positive displacement pump, and a monitoring device wherein the components are assembled to form a drainage system that functions to actively drain CSF from the ventricles of the brain of a patient when implanted in a patient, and wherein the pump is controlled based at least in part on at least one control factor that is monitored by the monitoring device. Another embodiment of a kit of the invention includes a ventricular catheter, a drainage catheter, a siphon control device, and a positive displacement pump that can function to actively drain CSF from the ventricles of the brain of a patient, wherein the components are assembled to form a drainage system that functions to actively drain CSF from the ventricles of the brain of a patient when implanted in a patient, and wherein the pump is controlled at least in part by the siphon control device. Another embodiment of a kit of the invention includes a ventricular catheter, a drainage catheter, a siphon control device, a bypass, a bypass valve, and a positive displacement pump that can function to actively drain CSF from the ventricles of the brain of a patient, wherein the bypass valve is disposed within the bypass when assembled, wherein the components are assembled to form a drainage system that functions to actively drain CSF from the ventricles of the brain of a patient when implanted in a patient, wherein the status of the bypass valve is actuated by the siphon control device, and wherein the CSF is directed through the bypass when the siphon control device detects overdrainage and through the distal catheter when the siphon control device detects a reversal of the overdrainage condition.

What is claimed is:

1. A drainage system for draining cerebrospinal fluid from a brain of a patient to a cavity of the patient, comprising:
   a ventricular catheter;
   a positive displacement pump operatively coupled to the ventricular catheter;
   a drainage catheter coupled to the positive displacement pump and establishing a drainage path, which is continually open, from the positive displacement pump to the cavity of the patient;
   a bypass fluidly coupled between the drainage catheter and the ventricular catheter;
   a bypass valve positioned within the bypass;
   a monitoring device configured to monitor at least one control factor; and
   a controller operatively coupled to the monitoring device and the positive displacement pump controlling the pump to regulate a flow of cerebrospinal fluid through the pump based at least in part on the at least one control factor.

2. The drainage system according to claim 1, wherein the pump is a diaphragm pump, a piston pump, a rotor pump, a peristaltic pump, or a screw pump.

3. The drainage system according to claim 2, wherein the pump is a peristaltic pump.

4. The drainage system according to claim 1, wherein the pump has a pumping rate of from about 1 ml/hr to about 200 ml/hr.

5. The drainage system according to claim 1, wherein the at least one control factor comprises symptoms or changes in symptoms of the patient, the time of day, circadian rhythms of the patient, the occurrence of various sleep patterns, the cardiac cycle, the position of the patient, the intracranial pressure of the patient, the degree of drainage of the ventricles of the patient or some combination thereof.

6. The drainage system according to claim 5, wherein the at least one control factor comprises the time of day.

7. The drainage system according to claim 5, wherein the at least one control factor comprises the position of the patient.

8. The drainage system according to claim 7, wherein the position of the patient is monitored with at least one accelerometer.

9. The drainage system according to claim 5, wherein the at least one control factor comprises intracranial pressure of the patient.

10. The drainage system according to claim 9, wherein the intracranial pressure of the patient comprises trends in intracranial pressure of the patient.

11. The drainage system according to claim 10 further comprising a sensor for intracranial pressure.

12. The drainage system according to claim 5, wherein the at least one control factor comprises the degree of drainage of the ventricles.

13. The drainage system according to claim 12, wherein the degree of drainage of the ventricles is monitored with a siphon control device.

14. The drainage system according to claim 13, wherein the siphon control device actuates the bypass valve which in turn effects flow through the bypass.

15. The drainage system of claim 13 wherein the siphon control device is coupled between the ventricular catheter and the positive displacement pump.

16. The drainage system according to claim 1, wherein the at least one control factor comprises symptoms or changes in symptoms of the patient, the time of day, circadian rhythms of the patient, the occurrence of various sleep patterns, the cardiac cycle, the position of the patient, the degree of drainage of the ventricles of the patient or some combination thereof.

* * * * *